United States Patent [19]

Cathcart

[11] Patent Number: 5,318,510
[45] Date of Patent: Jun. 7, 1994

[54] COLLECTION DEVICE

[75] Inventor: Bruce C. Cathcart, Lincoln, R.I.

[73] Assignee: Deknatel Technology Corporation, Inc., Fall River, Mass.

[21] Appl. No.: 714,546

[22] Filed: Jun. 11, 1991

[51] Int. Cl.⁵ .............................................. A61M 5/00
[52] U.S. Cl. ......................................... 604/4; 604/6; 604/317
[58] Field of Search ................... 604/4, 5, 6, 7, 19, 604/27, 46, 47, 317, 322, 318, 319, 320, 321

[56] References Cited

U.S. PATENT DOCUMENTS

| | | |
|---|---|---|
| Re. 29,877 | 1/1979 | Kurtz et al. |
| 3,363,626 | 1/1968 | Bidwell et al. |
| 3,363,627 | 1/1968 | Bidwell et al. |
| 3,507,395 | 4/1970 | Bentley |
| 3,559,647 | 2/1971 | Bidwell et al. |
| 3,683,913 | 8/1972 | Kurtz et al. |
| 3,765,536 | 10/1973 | Rosenberg |
| 3,765,537 | 10/1973 | Rosenberg |
| 3,768,653 | 10/1973 | Brumfield |
| 3,782,497 | 1/1974 | Bidwell et al. |
| 3,891,416 | 6/1975 | Leonard et al. |
| 3,993,461 | 11/1976 | Leonard et al. |
| 4,014,329 | 3/1977 | Welch et al. ............... 604/4 |
| 4,054,523 | 10/1977 | Ingemito et al. |
| 4,157,965 | 6/1979 | Raible |
| 4,164,468 | 8/1979 | Raible |
| 4,208,193 | 6/1980 | Munsch et al. |
| 4,243,531 | 1/1981 | Crockett et al. |
| 4,258,824 | 3/1981 | Kurtz et al. |
| 4,443,220 | 4/1984 | Hauer et al. |
| 4,642,089 | 2/1987 | Zupkas et al. |
| 4,662,906 | 5/1987 | Matkevich et al. |
| 4,664,682 | 5/1987 | Monzen |
| 4,704,203 | 11/1987 | Reed |
| 4,737,139 | 4/1988 | Zupkas et al. |
| 4,743,371 | 5/1988 | Servas et al. |
| 4,756,501 | 7/1988 | Quercia et al. |
| 4,784,642 | 11/1988 | Everett, Jr. et al. |
| 4,923,438 | 5/1990 | Vasconcellos et al. |
| 4,955,873 | 9/1990 | Rajlevsky |
| 4,955,874 | 9/1990 | Farrar et al. |
| 5,024,613 | 8/1991 | Corey, Jr. ............... 604/4 X |
| 5,078,677 | 1/1992 | Gentelia et al. ............... 604/4 |
| 5,116,308 | 5/1992 | Hagiwara ............... 604/4 |
| 5,127,900 | 7/1992 | Schickling et al. ............... 604/4 |

OTHER PUBLICATIONS

"Gish-ATR ™ - Blood Recovery/Autotransfusion System Directions For Use ATR-300 I.C.U. PAK", Gish Biomedical, Inc.

"CAPIOX® Cardiotomy Reservoir with Filter", Terumo Corporation, 1988, Japan.

"The Bard® William Harvey® H-4700", Bard Cardiosurgery Division, C. R. Bard, Inc.

"Shiley A Pfizer Company®—3L CARDF PLUS'-'—3 Liter Cardiotomy Reservoir with Filter, ©Shiley Incorporated, 1984.

"Hemodynamic DUO—A Cardiotomy Reservoir in the O.R. by Day. A Pleural Drainage Autotransfusion System in I.C.U. by Night.", ©Jul. 1987, Gish Biomedical, Inc.

(List continued on next page.)

Primary Examiner—Robert A. Hafer
Assistant Examiner—Sam Rimell
Attorney, Agent, or Firm—Pennie & Edmonds

[57] ABSTRACT

A collection device for receiving, collecting and returning blood from a body cavity, includes a housing for collecting the blood which has an inlet for fluid communication with the body cavity, a first outlet for returning blood to the body and a second outlet for coupling to a suction source. The collection device also includes a flow member which is configured and dimensioned so as to be disposed within the housing and so as to direct at least a portion of the blood entering through the inlet into a first predetermined direction and the remaining portion of the blood entering through the inlet and the first directed portion of blood in at least a second predetermined direction within the housing. The flow member can be a plate with ribs thereon to divert the flow of blood along the direction of the ribs. The collection device can also include a filter assembly positioned within the housing and about the plate so as to filter and defoam the blood before exiting from the housing.

6 Claims, 10 Drawing Sheets

OTHER PUBLICATIONS

"Bard® William Harvey® H-4700 Series Cardiotomy Reservoir Filtered/Biothyl Coated Model (Herparin Complex)" Bard Cardiosurgery Division, C. R. Bard, Inc.

"COBE—Perfusion Control System", ©1988 COBE Laboratories, Inc.

"Principles and Benefits of Cardiotomy Reservoirs—Baxter".

"Bentley® CATR®-3500 Cardiotomy/Autotransfusion Reservoir with Filter—A safe, cost-effective dual purpose reservoir system for improved cardiac patient care", ©Copyright 1988, Baxter Healthcare Corporation.

"Maxima® Hardshell ™ Venous Reservoir", ©Copyright 1989 Medtronic, Inc.

William Harvey® H-700 Series Cardiotomy Reservoir, Bard Cardiopulmonary Division, C. R. Bard, Inc.

"CFP3, CARD3L Cardiotomy Reservoirs (3 Liter)", ©Shiley Incorporated 1987.

"CATR ™ Cardiotomy Autotransfusion Reservoir System", Bentley®.

Cardiotomy Autotransfusion Pleural Drainage Reservoir With Integral Water Seal/Water Manometer, Gish–Cap ™.

COLLECTION DEVICE

TECHNICAL FIELD

The present invention relates to fluid collection devices and in particular to collection systems with separable reservoirs for removal and collection of fluids or gases from patients, such as from the chest cavity, by means of pressure differentials, and for possible return to the patient.

BACKGROUND ART

Drainage containers have been known for use in various medical procedures. For many years, the standard apparatus for performing the evacuation of the pleural cavity was a collection system known as the "3-bottle set-up" which includes a collection bottle, a water seal bottle and a suction control bottle. A catheter runs from the patient's pleural cavity to the collection bottle, and the suction bottle is connected by a tube to a suction source. The three bottles are connected in series by various tubes to apply suction to the pleural cavity to withdraw fluid and air and thereafter discharge the same into the collection bottle. Gases entering the collection bottle bubble through water in the water seal bottle. The water in the water seal also usually prevents the back flow of air into the chest cavity.

The 3-bottle set-up lost favor with the introduction of an underwater seal collection system sold under the name "Pleur-evac" ® in 1966 by Deknatel Inc. (a more detailed description of the need for and the proper use of chest collection devices is presented in the Deknatel Inc. Pleur-evac ® publication entitled "Physiology of the Chest and Thoracic Catheters: Chest Drainage Systems No. 1 of a series from Deknatel" (1985) which is incorporated herein in its entirety). U.S. Pat. Nos. 3,363,626; 3,363,627; 3,559,647; 3,683,913; 3,782,497; 4,258,824; and Re. 29,877 are directed to various aspects of the Pleur-evac ® system which over the years has provided improvements that eliminated various shortcomings of the 3-bottle set-up. These improvements have included the elimination of variations in the 3-bottle set-up that existed between different manufacturers, hospitals and hospital laboratories. Such variations include bottle size, tube length and diameter, stopper material and the like.

Among the features of the Pleur-evac ® system which provide its improved performance are employment of 3-bottle techniques in a single, pre-formed, self-contained unit. The desired values of suction are generally established by the levels of water in the suction control bottle and the water seal bottle. These levels are filled according to specified values prior to the application of the system to the patient. A special valve referred to as the "High Negativity Valve" is included which is employed when the patient's negativity becomes sufficient to threaten loss of the water seal. Also, a "Positive Pressure Release Valve" in the large arm of the water seal chamber works to prevent a tension pneumothorax when pressure in the large arm of the water seal exceeds a prescribed value because of suction malfunction, accidental clamping or occlusion of the suction tube. The Pleur-evac ® system is disposable and helps in the battle to control cross-contamination.

Despite the advantages of the Pleur-evac ® system over the 3-bottle set-up and the general acceptance of the device in the medical community, there remains a continuing need to improve the convenience and performance of chest collection systems and to render such systems compact.

Also, in a number of surgical procedures referred to in the art as cardiopulmonary bypass operations, it is necessary to interrupt and suspend the normal functioning of the patients's heart and lungs and to temporarily replace the function of these organs with artificial blood handling and treating units in a life-sustaining extracorporeal blood flow circuit. In these procedures, the main body of the patient's blood, which is called the venous return stream, is typically withdrawn from the patient through a venous cannula inserted into the right atrium, collected in a venous reservoir, and then passed through a blood pump (artificial heart), blood oxygenator (artificial) lung) and arterial blood filter before being returned to the patient through an aortic cannula inserted into the aorta distal to the aorta arch. In conventional practice, the venous reservoir is a flexible transparent bag with a blood outlet in the bottom. Additionally, in typical practice, patient's blood from the surgical field, which is called cardiotomy blood, is gathered in one or more cardiac vacuum suckers and defoamed, filtered and collected in a cardiotomy reservoir and filter device. The treated cardiotomy blood is then conducted to the venous reservoir, where it is combined with the venous return blood.

In addition, blood supplied to a patient must usually be purified by filtration to avoid jeopardizing the patient. The blood may be obtained from the patient during various surgical procedures when it is advantageous to store excess blood outside the body to facilitate the surgical procedures, or in blood conservation by scavenging the blood from the wound. Such blood is usually collected in a cardiotomy reservoir and purified there by passage through a filter unit within the reservoir. The blood passing through the cardiotomy reservoir must not only be purified of undesirable particulate matter such as surgical debris, but must also be freed of entrained air bubbles before being returned to the patient.

It is known to provide in a cardiotomy reservoir a filter unit including means for screening out particulate ma means for defoaming the blood to remove the air trapped therein. Examples of such known devices include those disclosed in U.S. Pat. Nos. 3,507,395 and 3,768,653. The former discloses a cardiotomy reservoir comprising a chamber containing a plate surrounded by a fibrous filter element contained in a nylon bag. The plate first spreads the incoming blood to remove the air bubbles therefrom which are vented, or drawn by vacuum, from the chamber, and the filter removes solid particles from the blood as it passes therethrough before leaving the chamber. U.S. Pat. No. 3,768,653 discloses a cardiotomy reservoir comprising a tubular chamber having a tangential inlet for the blood which is directed onto a filter across one end of the chamber which also contains a conical air filter.

Many other filtration systems are known for filtering blood and many use multiple layer elements to remove unwanted materials from the blood as it passes through the layers. U.S. Pat. No. 3,765,536 and U.S. Pat. No. 3,765,537 disclose a multiple layer blood filter elements including one comprising a first layer of coarse polypropylene netting, a second downstream layer of open-mesh polyester, a third spacer layer of polypropylene netting, a fourth microporous layer and a fifth polypropylene netting spacer layer.

I have invented an improved reservoir for use alone or with a collection device which provides additional improvements to presently available containers.

SUMMARY OF THE INVENTION

The present invention is directed to an apparatus for receiving fluids from a patient, comprising housing having an inlet for entry of fluids into the housing and an outlet for exit of fluids from the housing; and flow means disposed within the housing for at least directing the fluids entering through the inlet to flow in at least a predetermined first direction and in a predetermined second direction. The flow means comprises first rib member disposed adjacent the inlet and being configured and dimensioned so that at least a first portion of fluid falls upon the first rib member and is thereby directed along the first predetermined direction; and second rib member disposed adjacent the first rib member and being configured and dimensioned so that the at least first portion of fluid and the remaining portion of the fluid entering through the inlet falls upon the second rib and is thereby directed along the second predetermined direction.

Preferably, the flow means comprises a plurality of rib members disposed adjacent the inlet and each other and being configured and dimensioned so as to provide a corresponding plurality of predetermined directions in which at least portions of the fluids can flow.

The apparatus further comprising defoamer means configured and dimensioned so as to be disposed within the housing and in fluid communication with the fluid directed by the flow means prior to passing through the outlet.

In a preferred embodiment, an apparatus for receiving at least blood from a body cavity, comprises housing for collecting at least blood from a body cavity, the housing including an inlet for fluid communication with the body cavity, the housing including a first outlet for returning blood to the body and a second outlet for coupling to a suction source; and flow means being configured and dimensioned so as to be disposed within the housing and so as to direct at least a portion of the blood entering through the inlet into a first predetermined direction and the remaining portion of the blood entering through the inlet and the first directed portion in at least a second predetermined direction within the housing.

The flow means comprises a plate member disposed adjacent the inlet and having a plurality of rib members disposed on the respective plate member so as to divert the flow of blood from the direction in which the blood enters the housing through the inlet in at least the first and the second predetermined directions.

The rib members can also be disposed on the respective plate member so as to direct the flow of blood in a corresponding plurality of predetermined directions. Preferably the rib members are disposed generally transversely to the plate member which has a plurality of apertures disposed so that each rib member has a corresponding aperture adjacent thereto and being generally upstream of the respective rib member.

The apparatus additionally comprises defoamer means configured and dimensioned so as to be disposed within the housing such that the blood passes through the defoamer means before exiting through the first outlet for return to the body. Also, the apparatus further comprises a mount therefor comprising first body member having a generally C- shaped first end portion configured and dimensioned for attachment to a support; and second body member having a first end portion which is configured and dimensioned to receive and retain the housing, the first body member and the second body member being coupled to each other at their respective second end portions for rotational relative movement in discrete.

The present invention also is directed to a collection device for receiving, collecting and returning bodily fluids, comprising reservoir including housing having an inlet for entry of fluids into the housing and an outlet for exit of fluids from the housing; and flow means disposed within the housing for at least directing the fluids entering through the inlet to flow in at least a predetermined first direction and in a predetermined second direction; and suction control means having a first outlet for fluidly communicating with the second outlet of the reservoir housing and having a second outlet for fluidly communicating with the ambient. Preferably, the flow means comprises a plurality of rib members disposed adjacent the inlet and each other and being configured and dimensioned so as to provide a corresponding plurality of predetermined directions in which at least portions of the fluids can flow.

The collection device further comprises seal means fluidly coupled between the reservoir and the suction control chamber so as to prevent back flow of air to the patient.

Additionally, defoamer means configured and dimensioned so as to be disposed within the housing is provided in fluid communication with the fluid directed by the flow means prior to passing through the outlet.

BRIEF DESCRIPTION OF THE DRAWINGS

The present invention is described in greater detail hereinbelow, with reference to the drawings wherein.

DESCRIPTION OF THE PREFERRED EMBODIMENTS

In the description which follows, any reference to either orientation or direction is intended primarily for the purpose of illustration and is not intended in any way as a limitation of the scope of the present invention.

Figure 1:
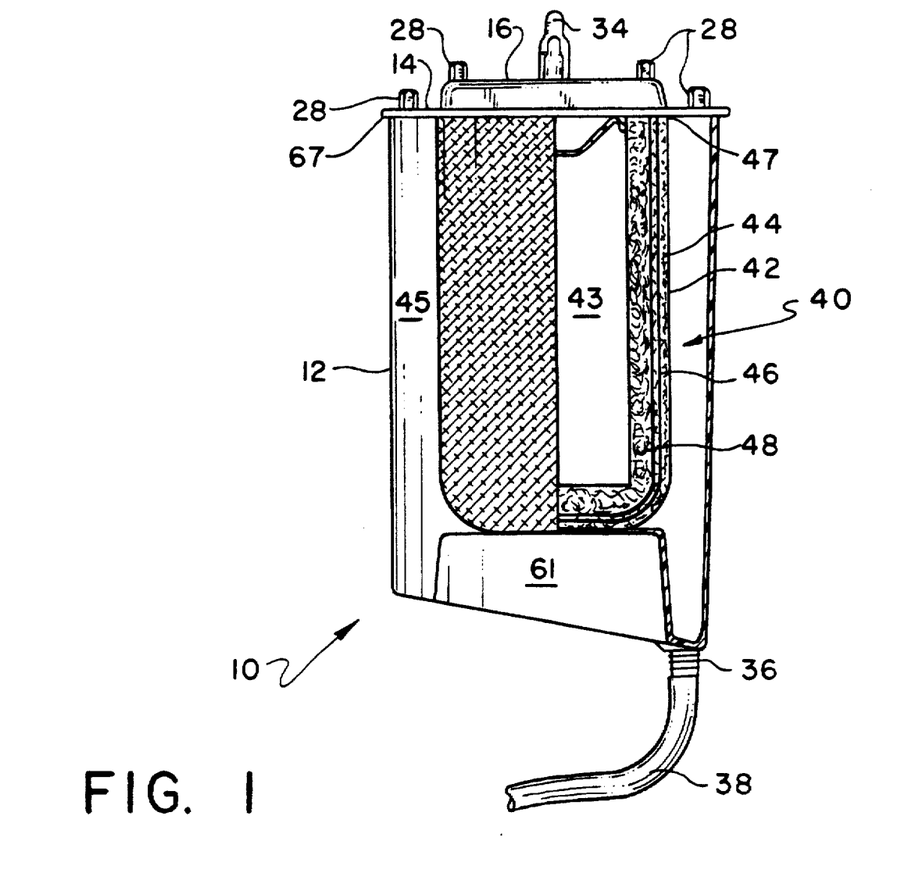
FIG. 1 is a front end view of a reservoir according to the present invention.
Figure 2:
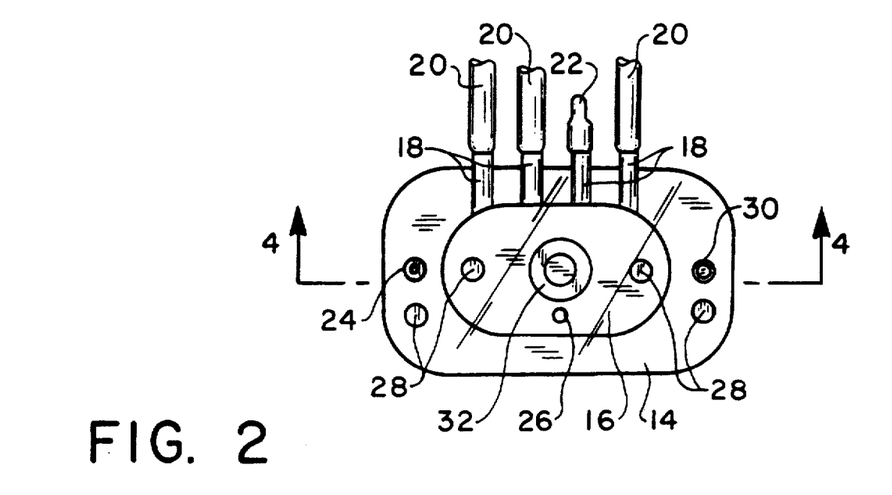
FIG. 2 is a top view of the reservoir of FIG. 1.

Referring to FIG. 1, a reservoir 10 according to the present invention, is formed of a housing 12 having a configuration as shown. The reservoir 10 has an upper open end which is closed by a cover 14 that has a raised central portion 16 as more clearly shown in FIG. 2. Four inlet ports 18 extend from the raised portion 16 three of which are shown coupled to suitable tubings 20 that can be coupled at their other end to the patient. One of the ports 18 is shown with a cap 22 which is provided with the reservoir prior to use. The raised portion 16 has a plurality of passageways therein which are coupled to the ports 18 and which ultimately couple with the interior of the housing 12. Such cap configuration is well known and is available in the Shiley "3L CARDF PLUS Cardiotomy Reservoir With Filter", hereinafter the Shiley reservoir. The cover 14 includes a vacuum or vent fitting 24 which allows for attachment to a vacuum source to provide suction at the ports 18 or allows pressure to be relieved from the reservoir 10 in the event that the ports 18 were connected to a pressure source such as a roller pump. A quick prime fitting 26 is provided on the raised portion 16 which allows, as described in more detail below, for conveniently priming the filter 40 with a fluid. A pair of leur fittings 28 positioned on the raised portion 16 and a second pair of leur fittings 28 positioned on the cover 14 provide inlets for adding solutions to the interior of the housing 12. A safety valve 30 allows excess positive pressure to be relieved from the reservoir 10 in the event that the vent/vacuum port 24 become occluded. The safety valve 30 will also allow atmospheric air to enter the reservoir 10 if excessive vacuum is drawn on the vent/vacuum port 24. A post operative collection inlet port 32 is positioned centrally of the raised portion 16 and allows blood to be collected post operatively through a patient tube. As shown in FIG. 1, the inner port 32 can be covered by a protective cap 34 when not in use. The inlet ports 18 are used for intraoperative blood collection with suction wands of the type known to those skilled in the art. The inlet ports 18 can also be used with ventricular vent devices.

Referring to FIG. 1, the housing 12 includes an exit port 36 which can be connected to a suitable tubing 38 that provides an outlet to the bypass circuit, for example, during bypass heart operations. In this manner, collected blood within the housing 12 can be returned to the cardiopulmonary bypass circuit or post operatively to continuously reinfuse the collected blood to the patient.

Positioned within the housing 12 is a filter and/or defoamer assembly 40 which both filters and defoams the collected blood within the housing 12. The filter or defoamer assembly 40 is generally similar to that which is found in the aforementioned Shiley reservoir and as generally discussed in U.S. Pat. Nos. 4,642,089, 4,737,139 and 4,743,371 which are incorporated herein in their entirety.

Figure 4:
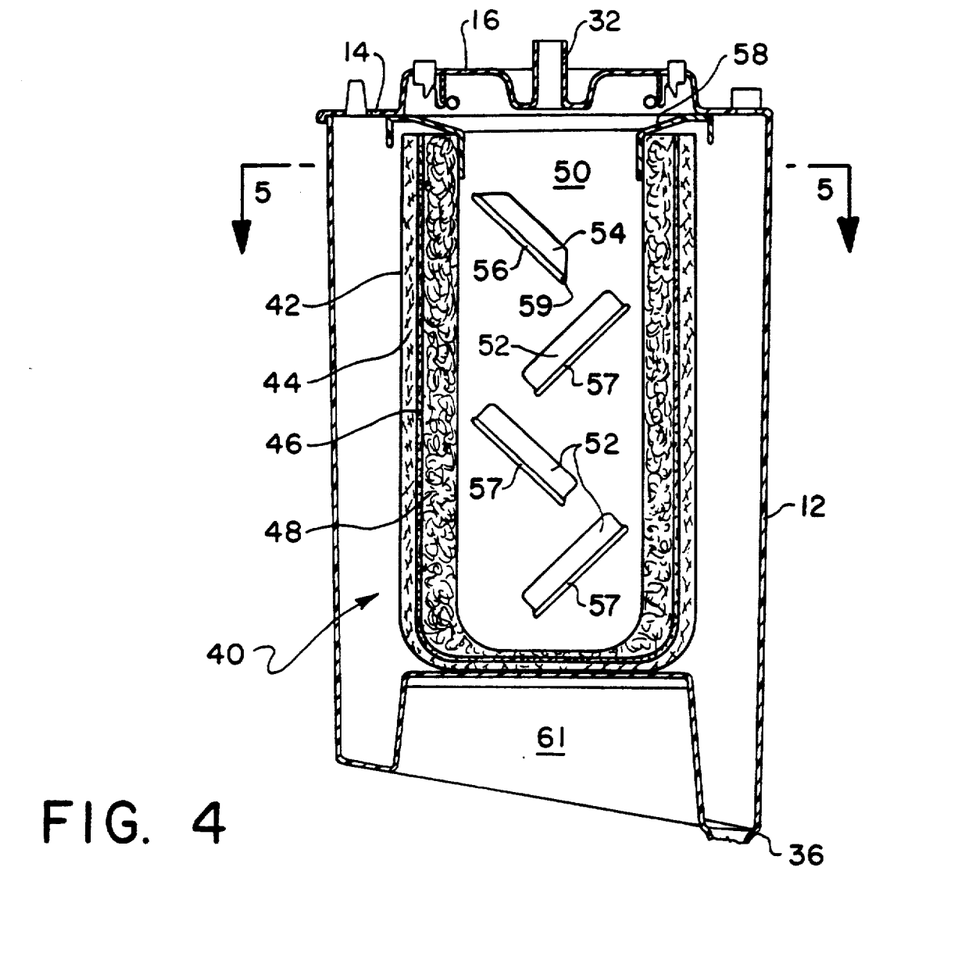
FIG. 4 is a cross-sectional view taken along the lines 4—4 of FIG. 2 of the reservoir according to the present invention.
Figure 5:
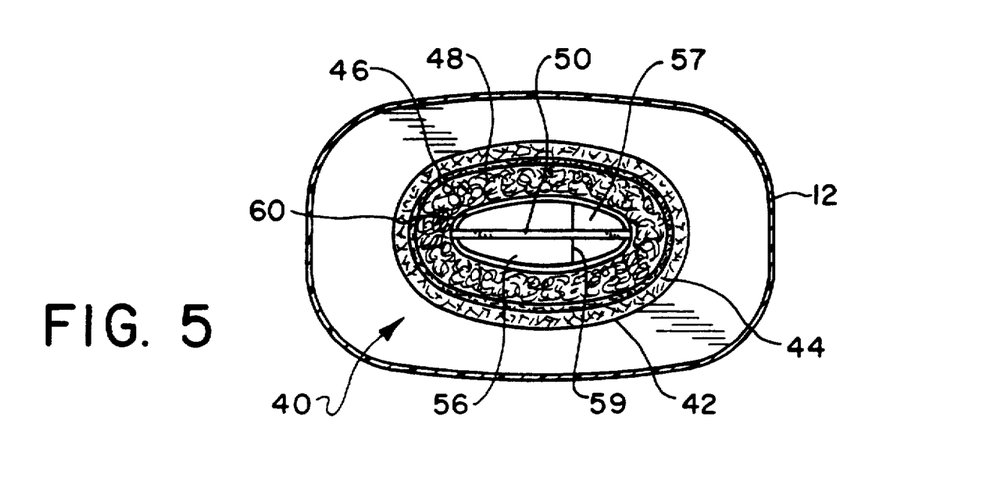
FIG. 5 is a cross-sectional view taken along the lines 5—5 of FIG. 4.
Figure 6:
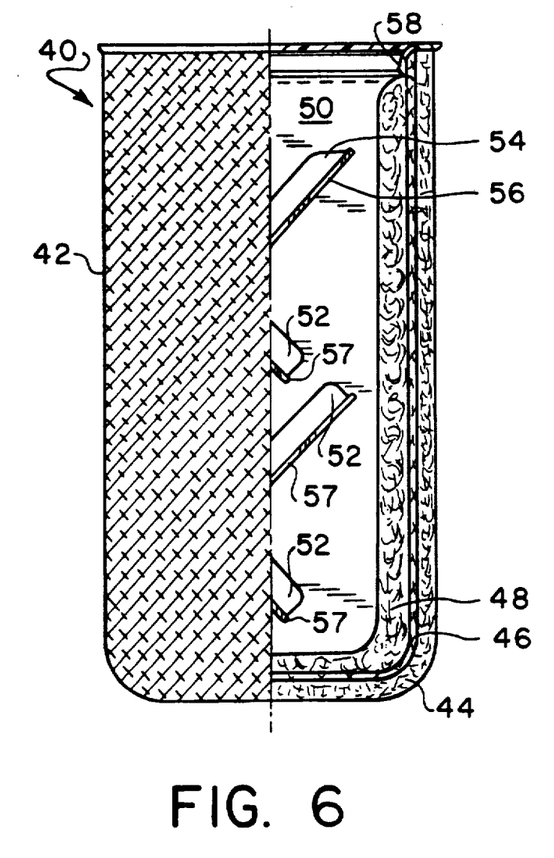
FIG. 6 is slightly enlarged and partially exposed view of the plate and rib member of the filter assembly of the reservoir according to the present invention.

The filter assembly 40, as shown particularly in FIGS. 1, 4 and 6, includes a polyester tricot outer sock 42 which encloses a quarter-inch foam member 44 having a porosity of 10 pores per inch (ppi). This, in turn, encloses a depth filter 46 which is formed of well-known filter material having about a 40 micron porosity. Next, a one-half inch foam 48 is positioned inwardly of the depth filter 46 and has a porosity of 30 ppi. The filter assembly 40 separates the housing 12 into an inner region 43 and an outer region 45 which itself is bounded by the wall of the housing 12.

Figure 7:
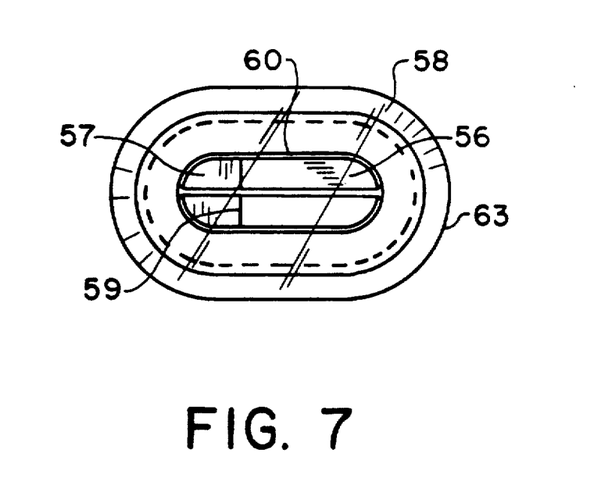
FIG. 7 is a top view of the filter assembly of FIG. 6.
Figure 9:
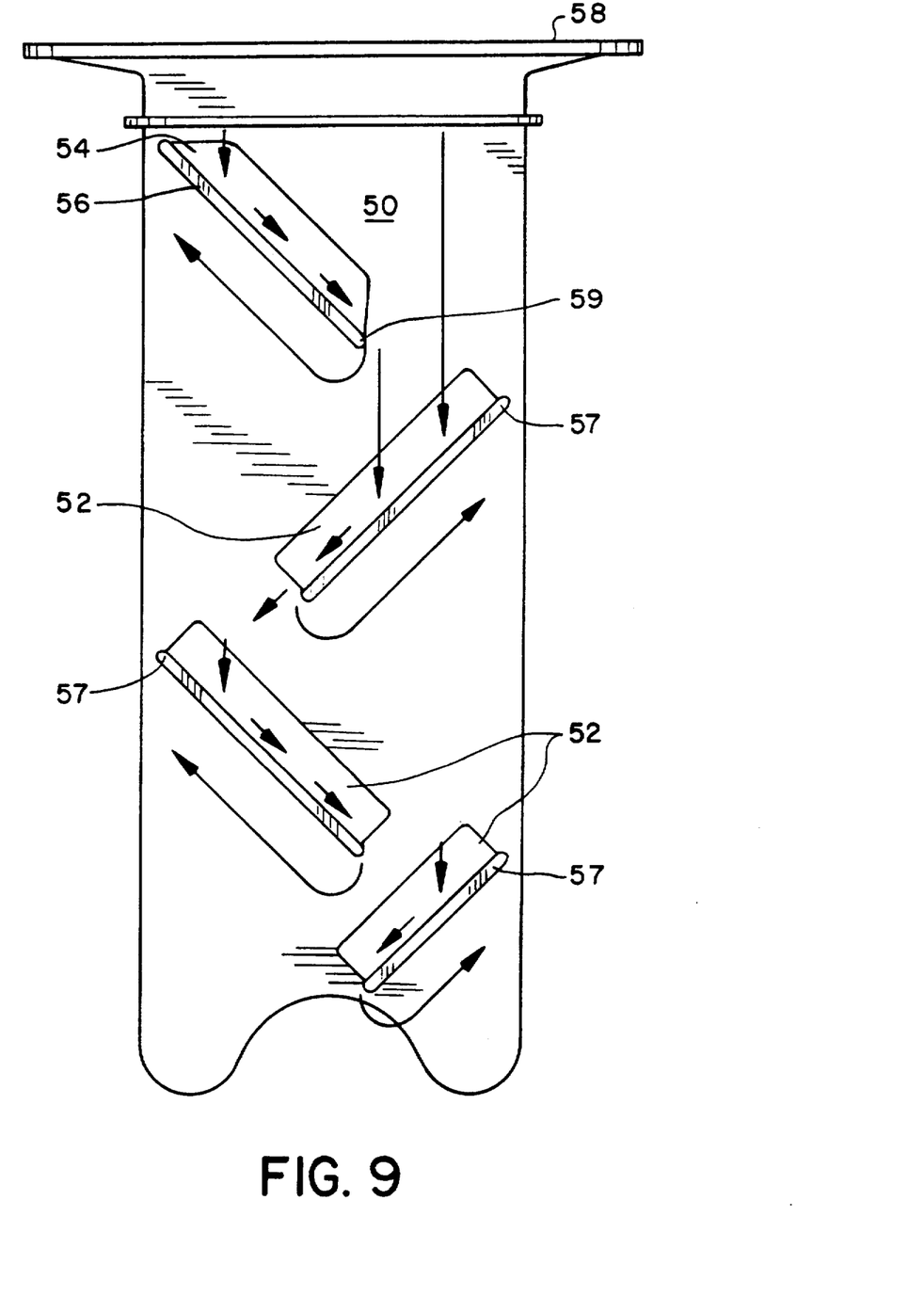
FIG. 9 is an enlarged side view of the plate member with ribs of the flow diverter according to the present invention illustrating the direction of the flow of fluids therealong.

The filter assembly 40 encloses a flow director which includes a rectangular plate member 50 which has three like configured apertures of a parallelogram configuration 52 and an upper aperture 54 which is of a trapezoidal configuration. Positioned within each aperture 52, 54 is a generally rectangular rib 56, 57 which extends laterally on both sides of the apertures 52, 54. Preferably, the ribs 56, 57 are transversely positioned relative to the plate member 50 in predetermined directions as shown in FIG. 9. The ribs 56, 57 can be glued or otherwise fastened within the apertures 52 or can be injection molded integrally with the plate member 50. The upstream portion of the plate member 50 is positioned within a funnel 58 as shown more clearly in FIGS. 6, 7 and 9 which, in turn, is positioned below the inlet ports that collectively converge upon the funnel 58. As shown in FIG. 7, the plate member 50 is positioned centrally of an oval opening 60 within the funnel 58, that generally slopes from its peripheral edge 63 down and inwardly in a downstream direction within the housing 12. As shown in FIG. 4, the open end of the filter assembly 40 is fitted up against the funnel 58 and secured thereabout by a tie wrap 47 as shown in FIG. 1. In this manner, inner region 43 is fluidly coupled to the ports 18 and the various inlets on the raised portion 16.

In operation, fluids including, for example, blood and/or gases from a patient will be collected through the tubings 20, through ports 18, through the common inlet within the raised portion 16 and down onto the funnel 58 which will thereby direct the fluid and blood and gases down through the opening 60 and onto the ribs 56, 57 in the direction of the arrows as shown in FIG. 9. As shown therein, some of the blood and gases will fall upon the first rib 56 positioned adjacent the funnel 58 and opening 60. Gases that are entrained within this fluid or blood will escape upwardly in the direction of the arrows as shown and can also pass through the apertures 52 and 54. Similarly, the blood can also pass through the apertures 52 and 54 depending on the orientation of the plate member 50 but will eventually fall upon at least one or more ribs 56. The first rib has a downstream edge 59. Thereafter, the portion of blood falling upon the first rib 56 will fall off the edge 59 onto the next adjacent rib 57 which will also receive the remaining blood passing through the opening 60. The blood falling together with the gases upon the second rib 57 will pass onto the third rib 57 and thereafter onto the fourth. If desired, additional ribs 57 can be provided in alternative orientations. Finally, the blood collected within the region 43 containing the plate member 50 will pass through the filter assembly 40 and into the region 45 between filter assembly 40 and the wall of housing 12. In this manner, the blood can be either stored or reinfused at the desired time to the patient through port 36 and tubing 38. The housing 12 also includes a recessed region 61 which allows the use of the reservoir with a collection device as will be discussed in greater detail hereinbelow.

Figure 3:
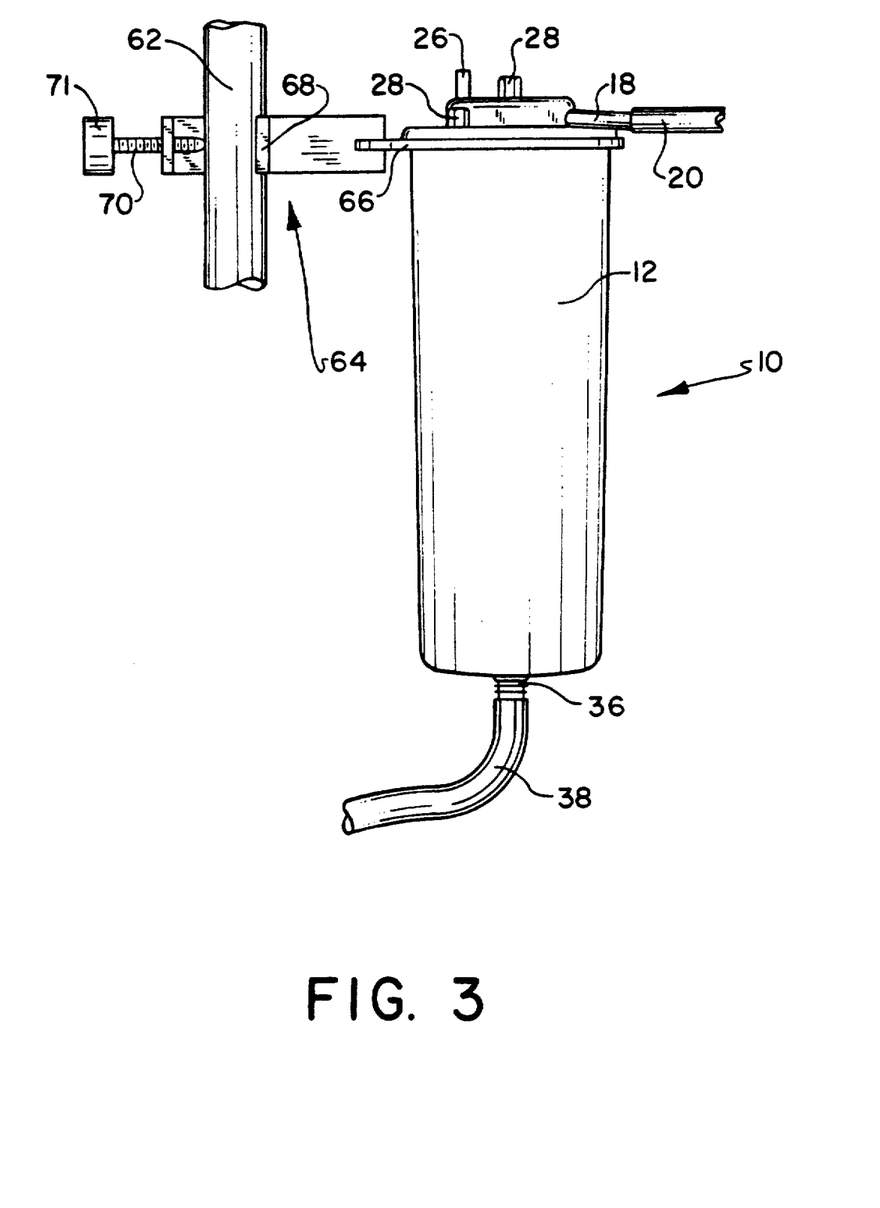
FIG. 3 is a side view of the reservoir of FIG. 1 supported in a hanging position with a pole mount according to the present invention.
Figure 15:
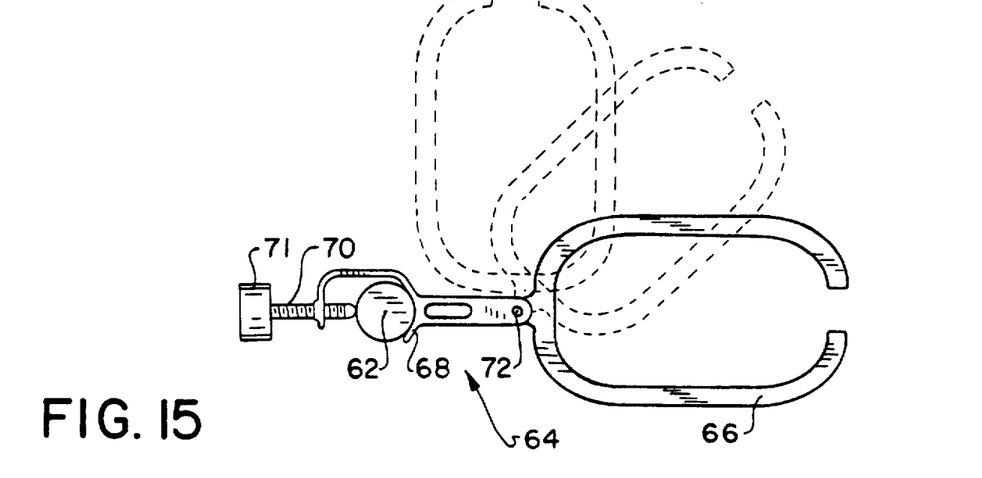
FIG. 15 is a top view of the pole mount in various operational positions according to the present invention.
Figure 16:
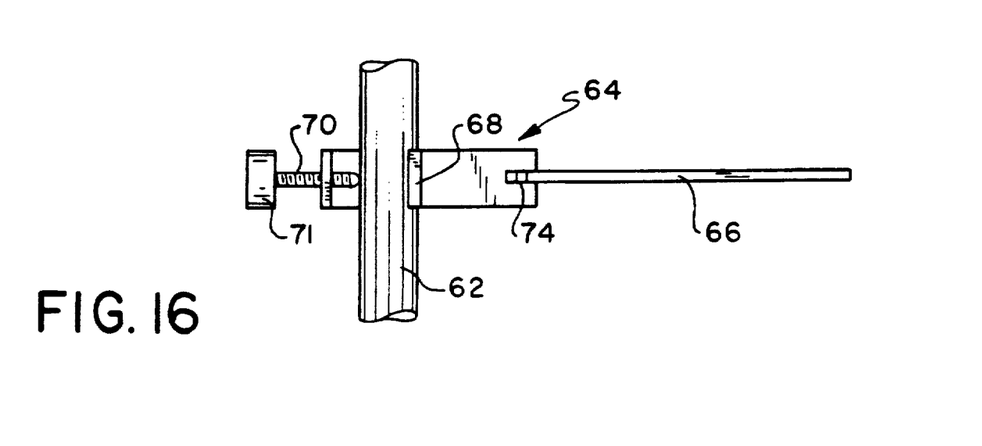
FIG. 16 is a side view of the pole mount of FIG. 15.
Figure 17:
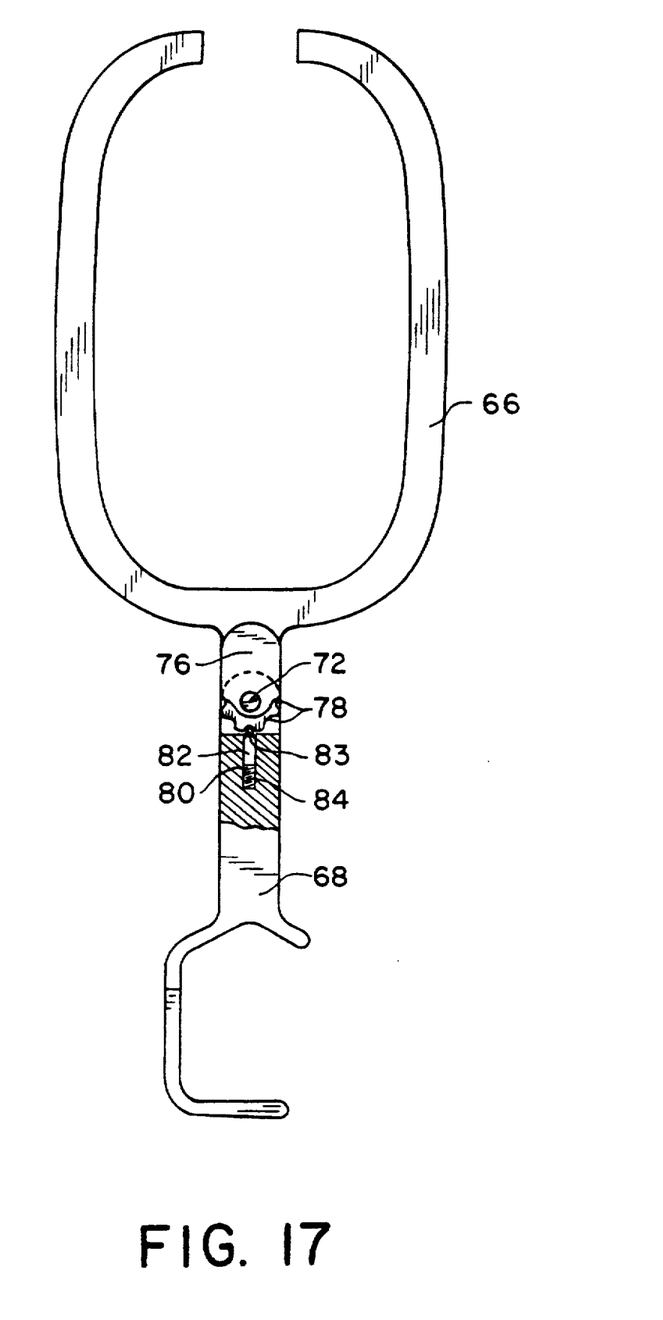
FIG. 17 is an enlarged and partially exposed top view of the pole mount of FIG. 15 illustrating the ratchet mechanism.

Referring to FIG. 3, the reservoir 10 is shown supported from a utility pole 62 by a pole mounting bracket 64. As shown more clearly in FIGS. 15-17, the utility pole mount 64 includes a generally U-shaped arm 66 which has an inner configuration suitable to receive the outer wall of housing 12. In addition, the cover 14 overhangs the housing 12 to provide a ledge 67 as shown in FIG. 1 and which is suitably sized so as to rest over the upper surface of the U-shaped arm portion 66. The utility pole bracket also includes a C-shaped clamp 68 which is positioned about the pole 62 and held thereto by a threaded bolt 70 with a knob 71. The bolt 70 passes through a like threaded bore (not shown) in the C-shaped clamp 68 and can be advanced by turning knob 71. The pole arm 66 and clamp 68 are pivotally or rotationally attached by a pin 72 which is press fitted through a bore in clamp 68 that lines up with a like sized bore in arm 66 when aligned as shown in FIG. 15. As shown in FIGS. 16 and 17, the clamp 68 has a recess 74 into which the stem 76 of arm 66 is positioned and held there in place by means of pin 72. The stem 76 ends in a series of spaced grooves 78. The clamp 68 has a passageway 80 which houses or receives a pin 82 with a reduced spherical end 83 and a spring 84 which biases the pin outwardly against the grooves 78 in stem 76. In this manner, the clamp 68 can be securely fastened to the pole 62 and the reservoir 10 can be retained within arm 66. Then, the arm 66 can be ratcheted by means of grooves 78 and pin 83 to a desired discrete position corresponding to the respective spaced grooves 78.

Figure 10:
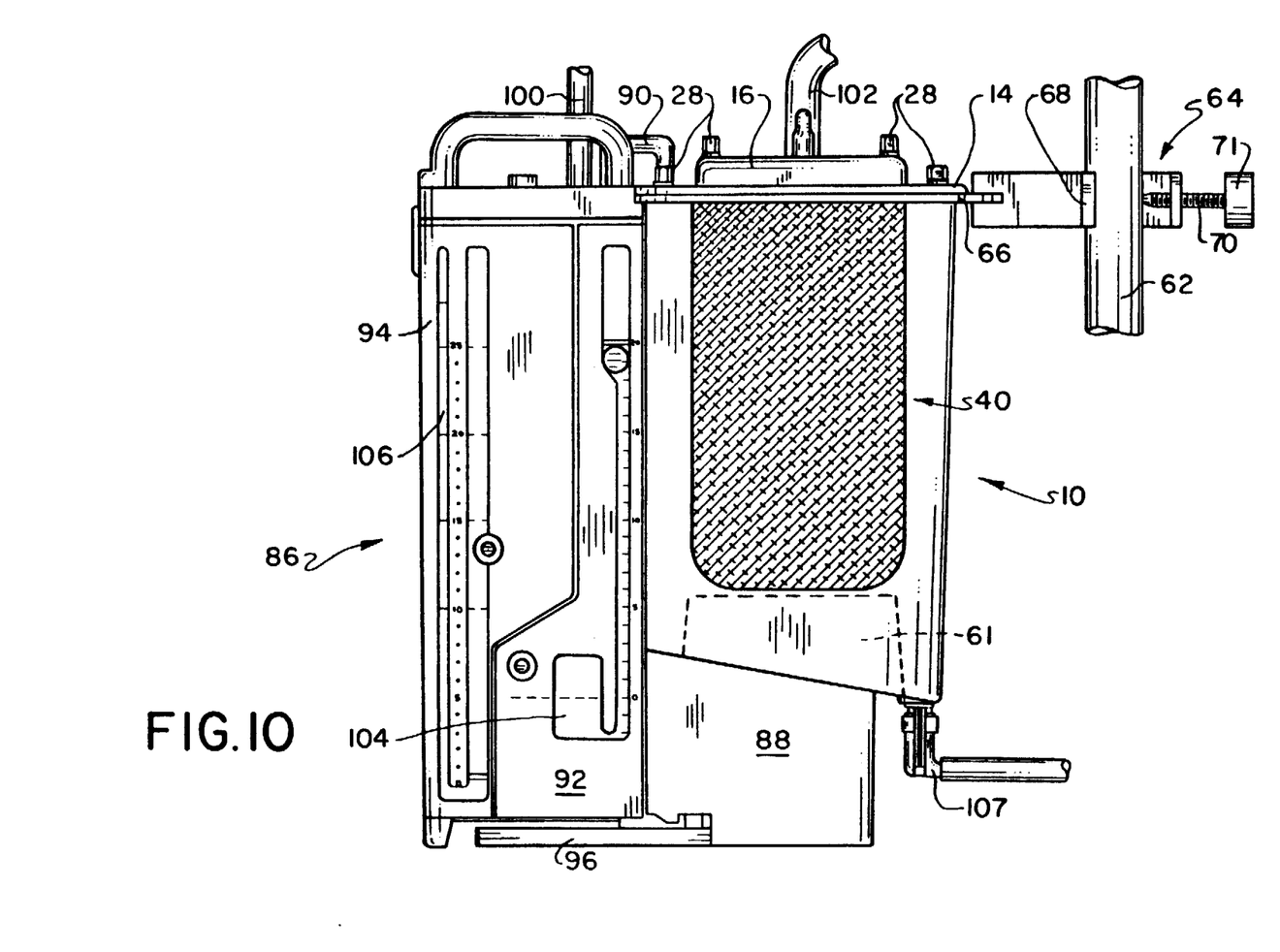
FIG. 10 is a front view of a collection/reservoir device supported in a hanging position with a pole mount according to the present invention.
Figure 11:
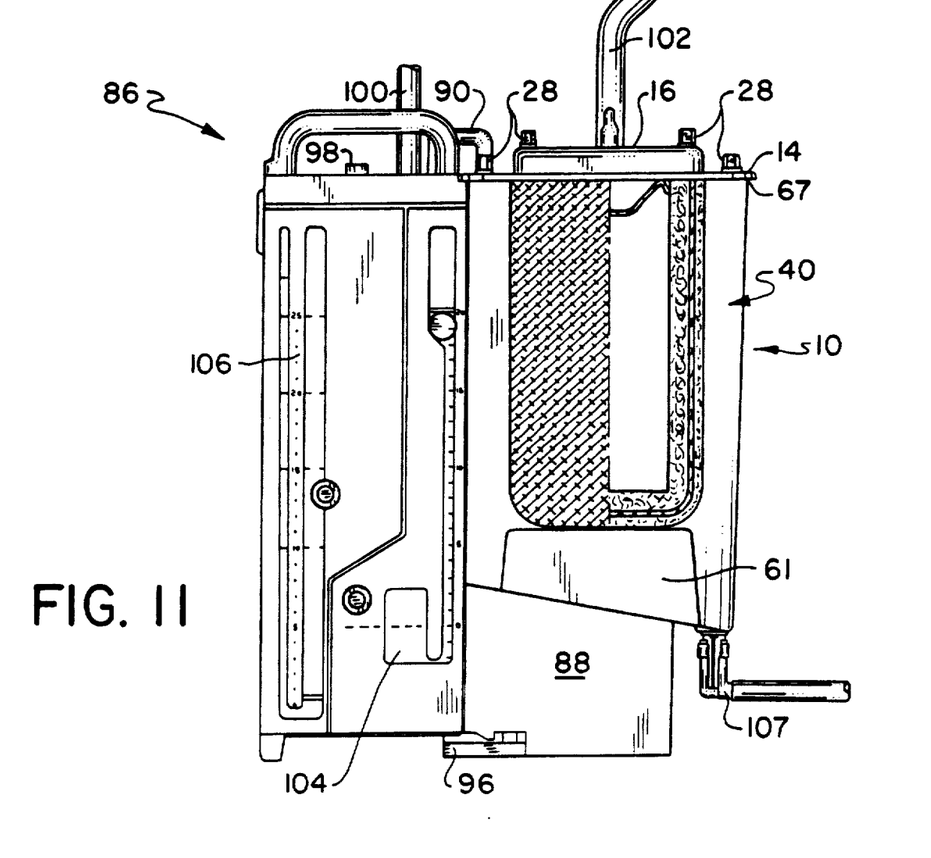
FIG. 11 is a front view of the collection/reservoir device of FIG. 10 illustrating a stabilizing support stand shown rotated to a locked operative body stabilizing position.
Figure 12:
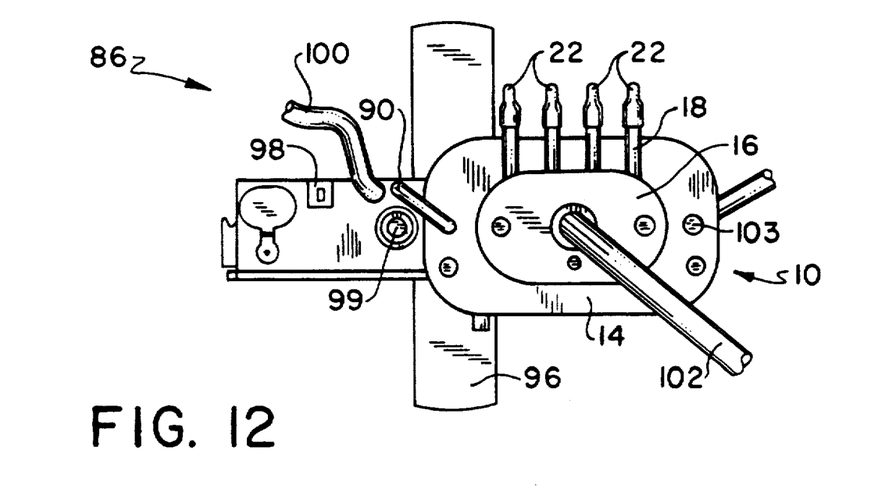
FIG. 12 is a top view of the collection/reservoir device of FIG. 11.

Referring to FIG. 10, an embodiment of the present invention is shown. In this embodiment, the reservoir 10 is supported by the pole mount 64 to a pole 62. The reservoir 10 is also coupled to a collection device 86 which has a pedestal 88 that is configured and dimensioned to be slotted within the recessed portion 61 of reservoir 10. The collection device 86 is generally of the type illustrated and discussed in U.S. Pat. Nos. 4,784,642 and 4,955,874 which are incorporated herein in their entirety. The operation and structure of such collection devices is set forth in the aforementioned patents. According to the embodiment of FIG. 10, the vent/vacuum port 24 is coupled by connected tubing 90 to collection device 86 and, in particular, to the water seal chamber portion 92. The collection device 86 also has a suction control chamber 94. In addition, the collection device 86 includes a floor stand 96 of the type shown and discussed in U.S. Pat. No. 4,955,873, which is also incorporated herein in its entirety. The floor stand or stabilizing member 96 can be rotated in the position as shown in FIG. 11 which illustrates the collection device 86 and reservoir 10 in a supported position on the floor. As shown in FIG. 12, the collection device 86 includes a positive pressure relief valve 98 and a high negativity relief valve 99 of the types which are generally known to those skilled in the art. The connector tubing 90 provides a jumper connection or a vacuum jumper between the reservoir 10 and the collection device or suction module 86. A tubing 100 from collection device 86 is coupled to a vacuum source (not shown) and provides suction into reservoir 10. The central port 32 is coupled to the patient by tubing 102. In the embodiment illustrated in FIG. 12, the cover 14 includes a safety check valve 103. As illustrated in FIGS. 10 and 11, the water seal 104 and the suction control manometer 106 are of the type generally discussed and illustrated in the aforementioned patents. Also, the outlet 36 on reservoir 10 in FIG. 10 is connected to the patient by a quick coupling connector 107 when utilized postoperatively unlike the tubing 38 of FIG. 1, which is used intraoperatively.

Figure 13:
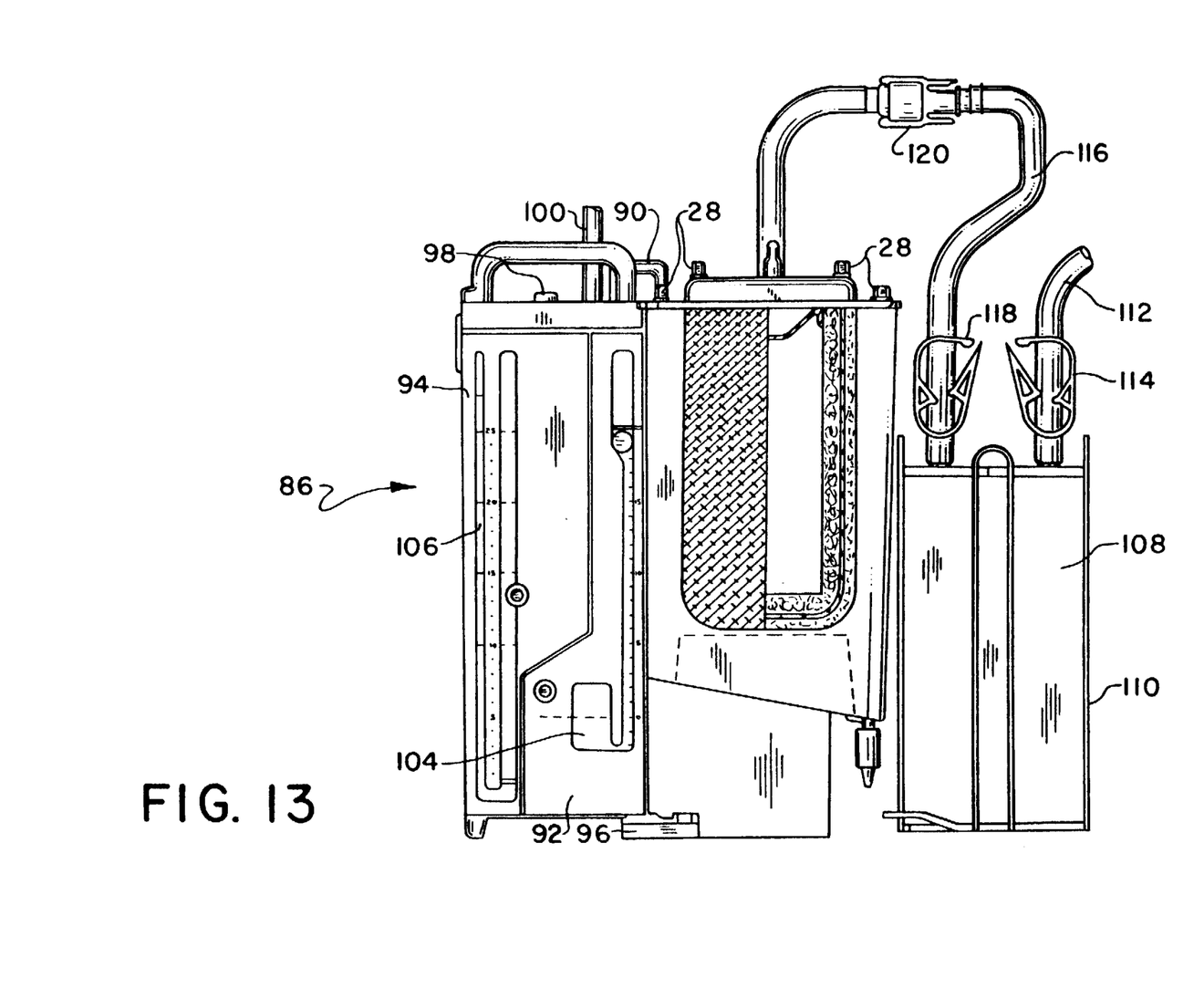
FIG. 13 is a front view of the collection/reservoir device of FIG. 10 coupled with a separate autotransfusion bag.
Figure 14:
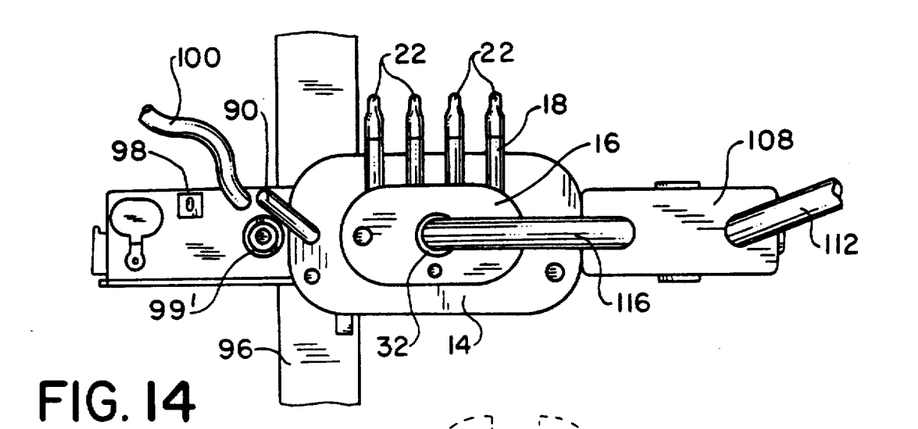
FIG. 14 is a top view of the collection/reservoir device and separate autotransfusion bag of FIG. 13.

Referring now to FIGS. 13 and 14, the reservoir 10 and collection device or suction module 86 of FIG. 11 in the floor stand supported configuration is illustrated together with an auto transfusion bag 108 which is supported within a frame 110. In this configuration, the autotransfusion inlet is coupled by tubing 112 to the patient. Flow through tubing 112 is controlled by a clamp 114. The suction is provided by means of tubing 116 which is controlled by clamp 118 and is ultimately coupled to the central port 32 and the raised section 16. The operation and structure of the autotransfusion bag are described and illustrated in U.S. Pat. Nos. 4,443,220 and 4,756,501 which are incorporated herein in their entirety. A coupling device 120 is shown in FIG. 13 and is of the type illustrated and described in commonly assigned U.S. Pat. No. 4,955,874 which is also incorporated in its entirety. The coupling device 120 provides a sampling injection port which allows for multiple hypodermic needle punctures while maintaining self-sealing capability.

In yet another alternative embodiment, the collection device 86 and reservoir 10 can be provided with hangers as described and illustrated in U.S. Pat. No. 4,756,501, which is incorporated in its entirety, so as to provide a hanging support from a horizontal rail.

Figure 8:
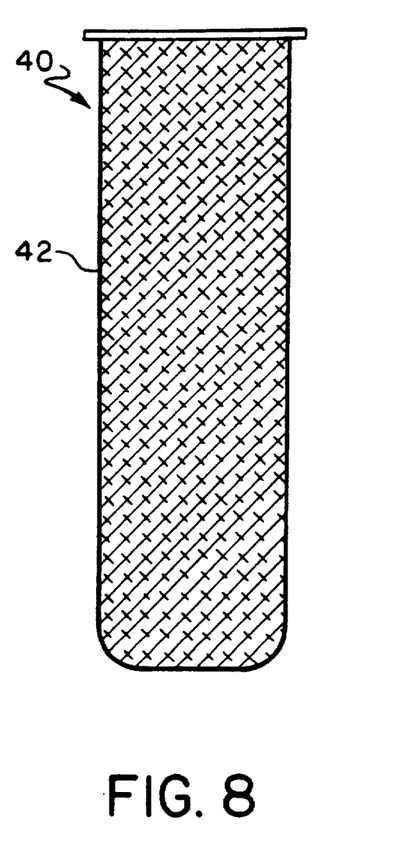
FIG. 8 is an end view of the filter assembly of FIG. 6.

As noted above regarding the operation of the reservoir 10, blood which enters through opening 60 is diverted from a unidirectional flow into various alternating paths providing gentle flow with minimal turbulence. In addition, such alternative paths allow for the escape of gases from the blood and fluids. Upon passage of the blood and fluids through the filter assembly 40, the filtered blood is available for return to the patient through the outlet port 36 in tubing 38 through a filter bypass circuit. In the configuration of the reservoir 10 employed with the collection device 86 in FIGS. 6-8, the reservoir can receive the fluids and blood and gases and upon filtration return the same immediately to the patient through the tubing 38. Alternatively, the exit port 36 can be sealed and the fluids collected within reservoir 10 until further need. In the case of collection from a plural cavity as described in U.S. Pat. No. 4,784,642, the reintroduction of fluids to the patient may be delayed in accordance with well-known medical procedures. Finally, in the configuration illustrated in FIG. 12, the reservoir 10 and collection device 86 can be incorporated with an autotransfusion bag 108 in a stand alone wire frame unit 110 similar to the manner shown and discussed in U.S. Pat. No. 4,756,501.

The present invention has been described in detail with particular emphasis on the preferred embodiments thereof. However, it should be understood that variations and modifications within the spirit and scope of the invention may occur to those skilled in the art to which the invention pertains.

I claim:

1. A collection device for receiving, collecting and returning bodily fluids, comprising:
   a. reservoir including:
      1. housing for collecting at least blood from a body cavity, said housing including an inlet for fluid communication with the body cavity, said housing including a first outlet for returning blood to the body and a second outlet for coupling to a suction source;
      2. flow means being configured and dimensioned so as to be disposed within said housing and so as to alternately direct at least a portion of the blood entering through said inlet along a first predetermined direction and the remaining portion of the blood entering through said inlet and the first directed portion along at least a second predetermined direction different than said first predetermined direction within said housing, wherein said flow means comprises a plate member disposed adjacent and generally downstream of said inlet and having a plurality of rib members disposed on said respective plate member along either the first predetermined direction or along the second predetermined direction different than said first predetermined direction so as to divert the flow of blood from the direction in which the blood enters the housing through said inlet along at least said first and said second predetermined directions
   b. suction control means having a first outlet for fluidly communicating with said second outlet of said reservoir housing and having a second outlet for fluidly communicating with the ambient.

2. The collection device according to claim 1 wherein said rib members are disposed on said respective plate member so as to direct the flow of blood in a corresponding plurality of predetermined directions.

3. The collection device according to claim 2 wherein said rib members are disposed generally transversely to said plate member.

4. The collection device according to claim 3 wherein said plate member has a plurality of apertures disposed so that each rib member has a corresponding aperture adjacent thereto and being generally upstream of said respective rib member.

5. The collection device according to claim 1 further comprising a seal means fluidly coupled between said reservoir and said suction control chamber so as to prevent back flow of air to the patient.

6. The collection device according to claim 1 further comprising defoamer means configured and dimensioned so as to be disposed within said housing and in fluid communication with the fluid directed by said flow means prior to passing through said outlet.

* * * * *